(12) United States Patent
Abe et al.

(10) Patent No.: US 8,227,238 B2
(45) Date of Patent: Jul. 24, 2012

(54) APPARATUS FOR PRODUCING PELLETS CONTAINING ENTRAPPED AND IMMOBILIZED MICROORGANISMS

(75) Inventors: Naoki Abe, Tokyo (JP); Koutarou Aoyama, Tokyo (JP); Tatsuo Sumino, Tokyo (JP); Hiroyoshi Emori, Tokyo (JP); Takayuki Kouno, Matsudo (JP)

(73) Assignee: Hitachi Plant Technologies, Ltd., Tokyo (JP)

( * ) Notice: Subject to any disclaimer, the term of this patent is extended or adjusted under 35 U.S.C. 154(b) by 531 days.

(21) Appl. No.: 12/382,340

(22) Filed: Mar. 13, 2009

(65) Prior Publication Data

US 2009/0197328 A1 Aug. 6, 2009

Related U.S. Application Data

(62) Division of application No. 11/445,189, filed on Jun. 2, 2006, now Pat. No. 8,030,041.

(30) Foreign Application Priority Data

Jun. 6, 2005 (JP) ................................. 2005-166045

(51) Int. Cl.
  *C12M 1/00* (2006.01)
  *C12N 11/02* (2006.01)
  *C12N 11/04* (2006.01)
  *C12N 1/04* (2006.01)

(52) U.S. Cl. ..................... 435/283.1; 435/177; 435/182; 435/260

(58) Field of Classification Search ........................ None
See application file for complete search history.

(56) References Cited

U.S. PATENT DOCUMENTS

| | | | |
|---|---|---|---|
| 4,727,030 A | 2/1988 | Ishimura et al. | |
| 7,568,643 B2 * | 8/2009 | Schoppel et al. | 241/84 |
| 7,794,590 B2 * | 9/2010 | Yoshikawa et al. | 210/151 |
| 7,816,110 B2 * | 10/2010 | Aoyama et al. | 435/182 |
| 7,842,185 B2 * | 11/2010 | Abe et al. | 210/601 |
| 7,897,042 B2 * | 3/2011 | Yoshikawa et al. | 210/151 |
| 2008/0230642 A1 | 9/2008 | Schoppel et al. | |

FOREIGN PATENT DOCUMENTS

| | | |
|---|---|---|
| EP | 0 060 052 A1 | 9/1982 |
| EP | 1 304 200 A1 | 4/2003 |
| JP | A-59-143587 | 8/1984 |
| JP | A 2-186987 | 7/1990 |
| JP | A 10-235384 | 9/1998 |
| JP | A-2003-000237 | 1/2003 |
| JP | A-2003-094082 | 4/2003 |
| JP | A 2003-235553 | 8/2003 |

OTHER PUBLICATIONS

Elvers et al; "Ullmann's Encyclopedia of Industrial Chemistry (Photography to Plastics, Processing) vol. A20 Ed. 5"; 1992; VCH Verlag; Weinheim (Germany); pp. 577-685.*
Office Action dated Dec. 22, 2010 in U.S. Appl. No. 11/445,189, filed Jun. 2, 2006.
The Condensed Chemical Dictionary, Eighth Edition, Van Nostrand Reinhold Co. New York, 1971, p. 545.
"Water treatment by microorganism immobilization method: Pellet immobilization method, entrapping immobilization method, biologically activated carbon method," published by NTS Inc., 2000.
Sumino et al., "Immobilization of Nitrifying Bacteria by Polyethylene Glycol Prepolymer," Journal of Fermentation and Bioengineering, vol. 73, No. 1, pp. 37-42, 1992.
Dec. 10, 2009 Office Action issued in U.S. Appl. No. 11/445,189.
Jun. 2, 2011 Patent Office Communication issued in U.S. Appl. No. 12/382,334.
May 31, 2011 Office Action issued in U.S. Appl. No. 12/382,334.
Apr. 27, 2012 Office Action issued in U.S. Appl. No. 12/662,614.

* cited by examiner

*Primary Examiner* — David Naff (74) *Attorney, Agent, or Firm* — Oliff & Berridge, PLC (57) ABSTRACT

A large amount of entrapping immobilization pellets with highly stable quality are produced inexpensively by high-speed treatment. There is provided a process for producing entrapping immobilization pellets in which microorganisms are entrapped and immobilized in an immobilizing agent, the process comprising polymerizing a mixture containing the microorganisms and a solution of the immobilizing agent in a forming frame into a gel to prepare a pellet block.

13 Claims, 11 Drawing Sheets

APPARATUS FOR PRODUCING PELLETS CONTAINING ENTRAPPED AND IMMOBILIZED MICROORGANISMS

This is a Division of application Ser. No. 11/445,189 filed Jun. 2, 2006 now U.S. Pat. No. 8,030,041, which claims the benefit of Japanese Patent Application No. 2005-166045 filed Jun. 6, 2005. The disclosures of the prior applications are hereby incorporated by reference herein in their entirety.

BACKGROUND OF THE INVENTION

1. Field of the Invention

The present invention relates to a process and an apparatus for producing entrapping immobilization pellets, entrapping immobilization pellets, and wastewater treatment equipment using the pellets. More particularly, the present invention relates to a process and an apparatus for producing entrapping immobilization pellets suitable for nitrification promoting advanced sewage treatment process in the field of wastewater treatment or the like.

2. Description of the Related Art

Nitrifying bacteria in activated sludge used for wastewater treatment grow slower than common bacteria. In particular, in winter during which water temperatures are low, such bacteria have only a small number of bacterial cells and thus exhibit significantly reduced nitrification activity. This tendency also applies to microorganisms having the same properties as in nitrifying bacteria. In this situation, there has been made an attempt to improve nitrification performance by attaching activated sludge containing nitrifying bacteria to the surface of an attachment material such as quartz sand, activated carbon, or plastic to increase the concentration of nitrifying bacteria (see "Water treatment by microorganism immobilization method: Pellet immobilization method, entrapping immobilization method, biologically activated carbon method," published by NTS Inc. in 2000). However, attachment immobilization pellets in which microorganisms are attached to an attachment material have a drawback in that the concentration of nitrifying bacteria cannot be sufficiently increased because the attached microorganisms are released from the material, or microorganisms differing from nitrifying bacteria as target microorganisms are attached to the pellets. Accordingly, wastewater has been treated at high speed with increased nitrification activity by producing entrapping immobilization pellets in which useful microorganisms such as nitrifying bacteria are immobilized in an immobilizing agent, and packing a wastewater treatment tank with the entrapping immobilization pellets to increase the concentration of nitrifying bacteria.

Entrapping immobilization pellets are produced by tube forming, dropping granulation, sheet forming or the like. Tube forming is a method comprising injecting a mixture of microorganisms with a polymer material into a vinyl tube with a diameter of several millimeters to polymerize and extrude the mixture, and cutting the mixture into cylindrical pellets with a certain length. This method can provide pellets with high form accuracy, but is not suitable for mass production. Dropping granulation is a method comprising dropping a mixture of microorganisms with a polymer material into a separate liquid to produce spherical pellets. This method allows easy mass production, but has a drawback in that the produced pellets have various particle sizes.

Figure 11:
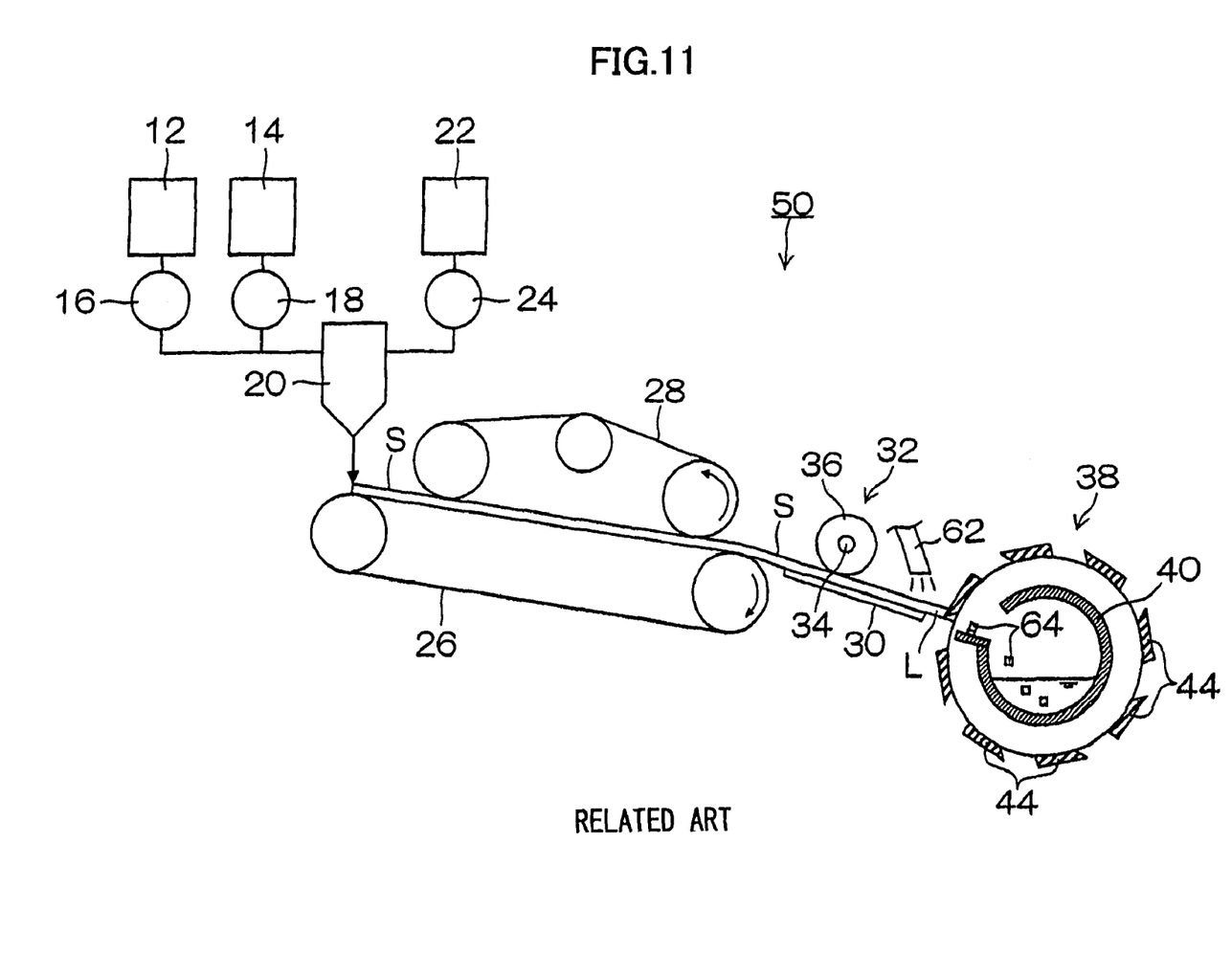
FIG. 11 is a view showing a configuration of a conventional apparatus for producing entrapping immobilization pellets.

As a device for solving these problems, Japanese Patent Application Laid-Open No. 2003-235553 discloses sheet forming comprising forming a mixture of microorganisms with a polymer material into a sheet, and finely cutting the sheet to produce rectangular pellets. In the sheet forming, as shown in FIG. 11, a raw material or chemical is cast into a space between belt conveyors 26, 28 by a stirring and extrusion unit 20, and is formed into a continuous sheet in the space between the belt conveyors. Then, the sheet is cut into lattices with a rotary blade 36 at certain intervals in the widthwise direction. Next, the lattice-shaped pellet block is cut into pellets 46 having a certain length using a guillotine cutting unit 38. This method can easily automate a granulation apparatus and provide a high form accuracy, and is thus assumed to be most suitable for mass granulation.

SUMMARY OF THE INVENTION

However, it is generally assumed that gel polymerization is preferably carried out in an atmosphere of an inert gas such as nitrogen, because oxygen in the air is reacted with a radical to inhibit curing. When a gel is prepared for electrophoresis in a laboratory, in order to prevent a gel solution from coming into contact with air and thereby oxidizing or inhibiting polymerization of the solution, a space between two plates or above the gel is charged with n-butyl alcohol to carry out polymerization or the like (see websites on the SDS-PAGE experimental method). However, since entrapping immobilization pellets are produced in a large amount, it is difficult in terms of cost to carry out the polymerization in an oxygen-free atmosphere as described above.

The sheet forming of Japanese Patent Application Laid-Open No. 2003-235553 has also a drawback in that polymerization is not stable and the pellets have reduced strength because the mixture has a large interface area in contact with air. Another drawback is that an unpolymerized substance remains on the sheet surface in contact with oxygen, and the unpolymerized substance is discharged as COD when the pellets are used for wastewater treatment. Since the formed sheet has unstable quality as described above, when wastewater treatment equipment is packed with entrapping immobilization pellets, the entrapping immobilization pellets cannot sufficiently exhibit their wastewater treatment performance in many cases.

The present invention has been achieved in view of such circumstances. An object of the present invention is to provide a process and an apparatus for producing entrapping immobilization pellets which can produce a large amount of entrapping immobilization pellets having highly stable quality inexpensively by high-speed treatment, entrapping immobilization pellets, and wastewater treatment equipment using the pellets.

According to a first aspect of the present invention, to attain the aforementioned object, there is provided a process for producing entrapping immobilization pellets in which microorganisms are entrapped and immobilized in an immobilizing agent, the process comprising polymerizing a mixture containing the microorganisms and a solution of the immobilizing agent in a forming frame into a gel to prepare a pellet block.

The present inventors have found that, in conventional sheet forming, the polymerization rate and the polymerization state differ between parts in contact with air and parts not in contact with air during gel polymerization, and thus the products have significantly different qualities. Specifically, the present inventors have found that, in conventional sheet forming, the mixture has a large area in contact with air, in particular, unpolymerized parts tend to appear on the surface of the mixture in contact with air, and the resulting pellets have different qualities.

The present invention reduces the interface of the mixture in contact with oxygen in the air by polymerization in the forming frame, and thus can produce entrapping immobilization pellets with highly stable quality. By employing a plurality of the forming frames, a large amount of entrapping immobilization pellets can be produced inexpensively at high speed. Further, since it is not necessary to replace the atmosphere in the polymerization step with a large volume of an inert gas, the production cost can be considerably reduced. The oxygen concentration in the forming frame may be further reduced by replacement with an inert gas.

In the first aspect, the forming frame is preferably made of a material that does not reduce activity of microorganisms, a material that does not inhibit polymerization reaction of the mixture, or a structure and a material in which oxygen or the like that inhibits polymerization reaction is hardly included. Specifically, a material that does not inhibit polymerization reaction of the mixture and has low wettability with the pellet block is preferable. For example, vinyl chloride, SUS, and an acrylic resin are more preferable. The pellet block polymerized in the forming frame having low wettability as described above can be smoothly removed from the forming frame with its shape maintained. In order to reduce the contact interface with oxygen, the forming frame preferably has a structure that can be closed with a lid or the like, or a structure having a small opening area for the mixture (corresponding to the bottom area) during polymerization, in particular. The shape of the forming frame (shape of the pellet block) is preferably a cuboid or cube from the viewpoint of handling, yield, and the like, but is not limited thereto. The shape may be a cylinder or the like. The pellet block refers to a pellet mass to be cut into substantially cubic entrapping immobilization pellets.

According to a second aspect of the present invention, there is provided the process for producing entrapping immobilization pellets according to the first aspect, wherein the pellet block has a deformation ratio of 50% or more. In the second aspect, the pellet deformation ratio is represented by the formula 1.

Pellet deformation ratio (%)=($H0-H1$)/$H0$×100 (Formula 1)

H0: Initial pellet thickness before compression, H1: Pellet thickness immediately before breakdown of pellet gel A deformation ratio of 50% in the second aspect means that the pellet block can be compressed to 50% of the initial thickness of entrapping immobilization pellets, and is broken down if further compressed.

When forming a pellet block using a forming frame, it is difficult to remove the block from the forming frame, resulting in a decrease in production efficiency. As a result of extensive studies in this situation for a technique of easily removing a pellet, the present inventors have found that the time for removing a pellet block largely depends on the deformation ratio of the pellet block. Specifically, a pellet having a small deformation ratio is attached to the forming frame and is set too much. Thus, the wall resistance between the forming frame and the pellet block is increased, making it difficult to remove the block from the frame. Further, a pellet having a too small deformation ratio is highly fragile (neither plastic nor ductile), and thus tends to be broken down even by a little external force.

In the second aspect, since the pellet has a deformation ratio of 50% or more, the pellet can be easily removed from the forming frame. When the pellet has a deformation ratio of 70% or more, the pellet can be more easily removed, favorably. As a result of extensive studies for controlling the deformation ratio of the pellet, the present inventors have found that a deformation ratio of 50% or more can be achieved using, as an immobilizing agent, a prepolymer having a molecular weight of 1,000 to 13,000 at a concentration per pellet of 3 to 10 mass %.

According to a third aspect of the present invention, there is provided the process for producing entrapping immobilization pellets according to the first or second aspect, wherein the mixture is heated to or maintained at a predetermined temperature during polymerization of the mixture.

As described above, when the mixture is polymerized in the forming frame, the mixture can be heated to or maintained at an appropriate temperature. Accordingly, in the reaction frame, the polymerization reaction rate can be controlled, and the reaction can be uniformly carried out.

According to a fourth aspect of the present invention, there is provided the process for producing entrapping immobilization pellets according to any one of the first to third aspects, wherein the mixture is polymerized for 10 to 60 minutes at a temperature of the forming frame of 20 to 30° C.

The polymerization temperature is a factor that affects the pellet strength and the polymerization rate. When the polymerization temperature is 20° C. or higher, the pellet strength is high in a substantially stable manner, and the polymerization rate is also high. However, when the polymerization temperature is higher than 30° C., the pellet strength and the polymerization rate almost do not change. On the other hand, when the polymerization temperature is lower than 20° C., the pellet strength is considerably reduced, and the polymerization rate is also reduced. Accordingly, the polymerization temperature is preferably 20° C. or higher, and more preferably 20 to 30° C.

When the polymerization time is longer than 60 minutes, the mixture is completely gelled, the forming frame has strong wall resistance, and thus the gel cannot be removed. On the other hand, when the time is shorter than 10 minutes, the mixture is insufficiently gelled, and it is thus difficult to remove the gel as a block. Accordingly, the present inventors have found that the block can be easily removed from the forming frame when polymerized at a polymerization temperature of 20 to 30° C. for a polymerization time of 10 to 60 minutes, although the appropriate polymerization time varies according to the polymerization temperature. With the polymerization temperature and the polymerization time of the present invention as described above, polymerization can be carried out for a short time to form a pellet block having an appropriate pellet strength.

According to a fifth aspect of the present invention, there is provided the process for producing entrapping immobilization pellets according to any one of the first to fourth aspects, further comprising: after preparing the pellet block in the forming frame, injecting a gas or liquid into the forming frame to remove the pellet block.

Depending on the material of the forming frame or the strength of the pellet block, it is difficult to remove the pellet block from the forming frame, disadvantageously, for example, a part of the pellet block remains in the forming frame. Thus, in the fifth aspect, by pressurizing an inside of the forming frame or injecting a liquid such as water into the frame to improve slip properties, the pellet block can be easily removed without damages. The removal time can also be reduced.

According to a sixth aspect of the present invention, there is provided the process for producing entrapping immobilization pellets according to any one of the first to fifth aspects, further comprising: cutting the pellet block into lattices while fixing a periphery of the pellet block; and then cutting the lattice-shaped pellet block substantially into cubes to provide pellets.

In the sixth aspect, the pellet block is first cut into lattices with, for example, lattice-shaped cutting blades, and then is cut perpendicular to the longitudinal direction with a rotary cutting blade. Thus, a large amount of uniform and substantially cubic pellets that have excellent form accuracy can be produced by high-speed treatment. Since the pellet block is cut while fixed, the pellet block is not deformed by pressure from the cutting blade. Accordingly, the pellet block can be cut into pellets with a uniform size without deformation of the cutting surfaces.

According to a seventh aspect of the present invention, there is provided the process for producing entrapping immobilization pellets according to any one of the first to sixth aspects, further comprising: controlling a transport speed of the pellet block and a speed of cutting the lattice-shaped pellet block substantially into cubes, so that the entrapping immobilization pellets after cutting are substantially cubes.

The general problem is that, when pellets not having a uniform shape are put into a wastewater treatment tank and used, the pellets clog a screen for preventing discharge of pellets or are discharged from the screen. Accordingly, pellets with a stable shape are required. In the seventh aspect, when the pellet block is cut while transporting the pellet block, the transport speed of the pellet block and the cutting speed of the lattice-shaped pellet block (corresponding to the rotation speed of the rotary cutting blade, for example) are controlled so that the resulting pellets are substantially cubes with a uniform size. Thus, a large amount of entrapping immobilization pellets having a stable shape can be produced.

According to an eighth aspect of the present invention, there is provided an apparatus for producing entrapping immobilization pellets, comprising at least one forming frame in which a mixture containing microorganisms and an immobilizing agent solution is polymerized into a gel to prepare a pellet block.

In the eighth aspect, the present invention is embodied as an apparatus in which a mixture containing microorganisms and an immobilizing agent solution is polymerized in at least one forming frame. The present invention reduces the interface of the mixture in contact with oxygen in the air by polymerization in the forming frame, and thus can prevent generation of an unpolymerized part. Accordingly, entrapping immobilization pellets with highly stable quality can be produced. By employing a plurality of the forming frames, a large amount of entrapping immobilization pellets can be produced inexpensively at high speed.

According to a ninth aspect of the present invention, there is provided the apparatus for producing entrapping immobilization pellets according to the eighth aspect, wherein the forming frame comprises a heating device.

By providing the heating device in the forming frame as described above, the mixture can be heated to or maintained at an appropriate temperature to carry out polymerization. Accordingly, in the reaction frame, the polymerization reaction rate can be controlled, and the reaction can be uniformly carried out.

According to a tenth aspect of the present invention, there is provided the apparatus for producing entrapping immobilization pellets according to the eighth or ninth aspect, further comprising: an extrusion device which extrudes the pellet block from the forming frame, wherein the extrusion device comprises at least one of an inclination device of inclining the forming frame and a pressurizing device of pressurizing an inside of the forming frame.

Depending on the material of the forming frame or the strength of the pellet block, it is difficult to remove the pellet block from the forming frame, disadvantageously, for example, a part of the pellet block remains in the forming frame. Thus, in the tenth aspect, by pressurizing the inside of the forming frame or injecting a liquid such as water into the frame to improve slip properties, the pellet block can be easily removed without damages. Accordingly, the removal time can be reduced.

According to an eleventh aspect of the present invention, there is provided the apparatus for producing entrapping immobilization pellets according to any one of the eighth to tenth aspects, further comprising lattice-shaped cutting blades of cutting the pellet block into lattices; and a rotary cutting blade of cutting the pellet block cut into lattices substantially into cubes, the blade provided downstream of the lattice-shaped cutting blades.

In the eleventh aspect, the pellet block is first cut into lattices, and then is cut perpendicular to the longitudinal direction with the rotary cutting blade. Thus, a large amount of uniform and substantially cubic pellets that have excellent form accuracy can be produced by high-speed treatment. Since the pellet block is cut while fixed, the pellet block can be left undeformed by pressure from the cutting blade.

According to a twelfth aspect of the present invention, there is provided the apparatus for producing entrapping immobilization pellets according to any one of the eighth to eleventh aspects, further comprising: a control device which controls a transport speed of the pellet block and a rotation speed of the rotary cutting blade, so that the entrapping immobilization pellets after cutting are substantially cubes.

The problem is that, when pellets not having a uniform shape are put into a wastewater treatment tank and used, the pellets clog a screen for preventing discharge of pellets or are discharged from the screen. Accordingly, pellets with a stable shape are required. In the twelfth aspect, when the pellet block is cut while transporting the pellet block, the pellet block is first cut into lattices with the lattice-shaped cutting blades while transporting the block. Next, the lattice-shaped pellet block is cut into blocks of entrapping immobilization pellets at certain intervals perpendicular to the longitudinal direction with the rotary cutting blade. In cutting the pellet block, by controlling the transport speed of the pellet block and the rotation speed of the rotary cutting blade, a large amount of substantially cubic entrapping immobilization pellets can be produced in a stable manner.

According to a thirteenth aspect of the present invention, there is provided the apparatus for producing entrapping immobilization pellets according to any one of the eighth to twelfth aspects, wherein the microorganisms are bacteria contained in activated sludge. Since activated sludge containing target microorganisms (such as nitrifying bacteria) as described above is used in a wastewater treatment process, a relatively large amount of microorganisms are available inexpensively.

According to a fourteenth aspect of the present invention, there is provided the apparatus for producing entrapping immobilization pellets according to any one of the eighth to thirteenth aspects, wherein the forming frame is substantially a cuboid or cube.

The entrapping immobilization pellets used in the present inventions are substantially cubes excellent in terms of stirring and flowability in a wastewater treatment tank. In the fourteenth aspect, since the shape of the pellet block is a cuboid or cube, a large amount of uniform and cubic entrapping immobilization pellets can be efficiently produced.

According to a fifteenth aspect of the present invention, there is provided the apparatus for producing entrapping immobilization pellets according to the fourteenth aspect, wherein the forming frame has a ratio V/S of the volume V to the bottom area S of 10 to 100.

In the fifteenth aspect, the shape of the forming frame is specified. By providing the pellet block with a shape defined by the present invention, the contact interface with oxygen (corresponding to the bottom area part) can be reduced, and the resistance when removing the block from the forming frame can also be reduced. Accordingly, entrapping immobilization pellets with highly stable quality can be efficiently produced. The shape of the forming frame is preferably a cuboid, a cube or the like, but is not limited thereto. The shape may be a cylinder or the like.

According to a sixteenth aspect of the present invention, there is provided entrapping immobilization pellets produced by the apparatus for producing entrapping immobilization pellets according to any one of the eighth to fifteenth aspects.

The entrapping immobilization pellets according to the sixteenth aspect are produced using the apparatus for producing entrapping immobilization pellets of the present invention. Thus, uniform and cubic entrapping immobilization pellets with highly stable quality can be obtained.

According to a seventeenth aspect of the present invention, there is provided a wastewater treatment equipment in which wastewater is treated with the entrapping immobilization pellets according to the sixteenth aspect.

According to the seventeenth aspect, entrapping immobilization pellets produced using the production apparatus of the present invention are put into a wastewater treatment tank to carry out wastewater treatment. Thus, microorganisms can be packed with the wastewater treatment tank at a high concentration, and wastewater can be efficiently treated.

As described above, the present invention can produce a large amount of entrapping immobilization pellets with highly stable quality inexpensively by high-speed treatment.

DETAILED DESCRIPTION OF THE PREFERRED EMBODIMENTS

Preferred embodiments of the process and the apparatus for producing entrapping immobilization pellets, the entrapping immobilization pellets, and the wastewater treatment equipment using the pellets of the present invention will be described below with reference to the accompanying drawings.

Figure 1:
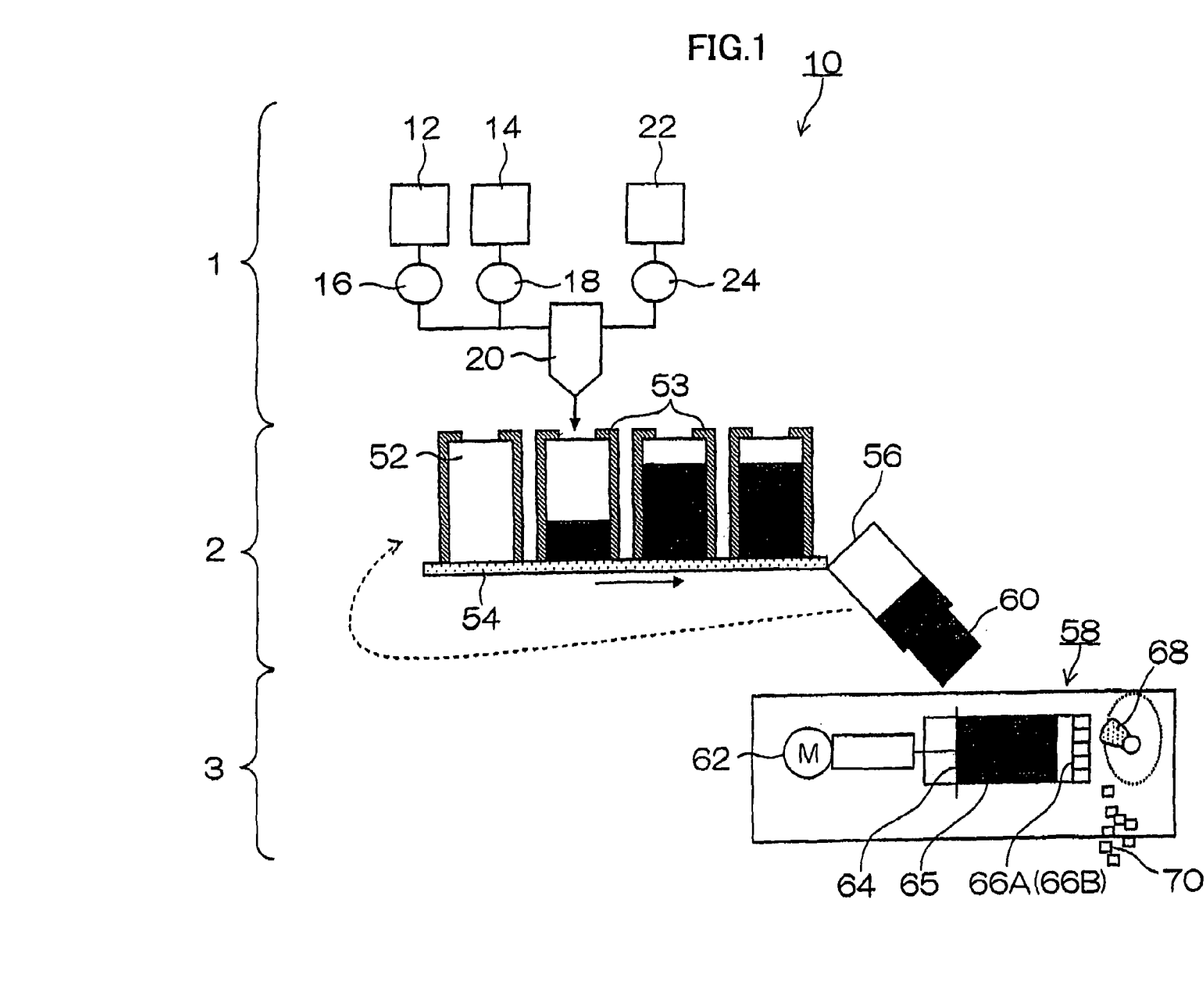
FIG. 1 is a plan view showing an entire configuration of the apparatus for producing entrapping immobilization pellets to which the present invention is applied.

FIG. 1 is a view showing an entire configuration of the production apparatus of the present invention. As shown in FIG. 1, the production apparatus 10 is configured to comprise a raw material mixing section 1, a pellet block preparation section 2, and a pellet block cutting section 3 as main components.

The raw material mixing section 1 comprises, as main components, a raw material tank 12 in which a raw material is stored, chemical tanks 14, 22 in which chemicals are stored, and a stirring and extrusion unit 20 in which the raw material is mixed with the chemicals.

In the raw material tank 12, microorganisms (activated sludge) as a raw material are stored. In the chemical tank 14, a chemical such as an immobilizing agent solution is stored. In the chemical tank 22, a chemical such as a polymerization initiator is stored.

Pumps 16, 18, 24 are driving devices of introducing the raw material in the raw material tank 12, the chemical in the chemical tank 14, and the chemical in the chemical tank 22 into the stirring and extrusion unit 20, respectively, and are provided between the stirring and extrusion unit 20 and the raw material tank 12, the chemical tank 14, and the chemical tank 22, respectively. Thus, a mixture as a raw material for producing entrapping immobilization pellets can be prepared in the stirring and extrusion unit 20 and extruded into a forming frame 52.

Microorganisms to be immobilized are bacteria contained in activated sludge, which are complex microorganisms comprising nitrifying bacteria, denitrifying bacteria, and anaerobic ammonium-oxidizing bacteria. In order to increase the initial immobilizing concentration of the target microorganisms, the activated sludge concentration is preferably 10,000 to 40,000 mg-ss/L. Pure microorganisms such as microcystis decomposing bacteria, PCB decomposing bacteria, dioxin decomposing bacteria, and environmental hormone decomposing bacteria can also be used.

Examples of immobilizing agent prepolymers and crosslinking agents that can be used in the present invention include the following compounds: monomethacrylates such as polyethylene glycol monomethacrylate, polyprene glycol monomethacrylate, polypropylene glycol monomethacrylate, methoxydiethylene glycol methacrylate, methoxypolyethylene glycol methacrylate, methacryloyloxyethyl hydrogen phthalate, methacryloyloxyethyl hydrogen succinate, 3-chloro-2-hydroxypropyl methacrylate, stearyl methacrylate, 2-hydroxy methacrylate, and ethyl methacrylate; monoacrylates such as 2-hydroxyethyl acrylate, 2-hydroxypropyl acrylate, isobutyl acrylate, t-butyl acrylate, isooctyl acrylate, lauryl acrylate, stearyl acrylate, isobornyl acrylate, cyclohexyl acrylate, methoxytriethylene glycol acrylate, 2-ethoxyethyl acrylate, tetrahydrofurfuryl acrylate, phenoxyethyl acrylate, nonylphenoxypolyethylene glycol acrylate, nonylphenoxypolypropylene glycol acrylate, silicon-modified acrylate, polypropylene glycol monoacrylate, phenoxyethyl acrylate, phenoxydiethylene glycol acrylate, phenoxypolyethylene glycol acrylate, methoxypolyethylene glycol acrylate, acryloyloxyethyl hydrogen succinate, and lauryl acrylate; dimethacrylates such as 1,3-butylene glycol dimethacrylate, 1,4-butanediol dimethacrylate, ethylene glycol dimethacrylate, diethylene glycol dimethacrylate, triethylene glycol dimethacrylate, polyethylene glycol dimethacrylate, butylene glycol dimethacrylate, hexanediol dimethacrylate, neopentyl glycol dimethacrylate, polyprene glycol dimethacrylate, 2-hydroxy-1,3-dimethacryloxypropane, 2,2-bis-4-methacryloxyethoxyphenylpropane, 3,2-bis-4-methacryloxydiethoxyphenylpropane, and 2,2-bis-4-methacryloxypolyethoxyphenylpropane; diacrylates such as ethoxylated neopentyl glycol diacrylate, polyethylene glycol diacrylate, 1,6-hexanediol diacrylate, neopentyl glycol diacrylate, tripropylene glycol diacrylate, polypropylene glycol diacrylate, 2,2-bis-4-acryloxyethoxyphenylpropane, 2-hydroxy-1-acryloxy-3-methacryloxypropane; trimethacrylates such as trimethylolpropane trimethacrylate; triacrylates such as trimethylolpropane triacylate, pentaerythritol triacylate, trimethylolpropane EO-added triacylate, glycerol PO-added triacylate, and ethoxylated trimethylolpropane triacylate; tetraacrylates such as pentaerythritol tetraacrylate, ethoxylated pentaerythritol tetraacrylate, propoxylated pentaerythritol tetraacrylate, and ditrimethylolpropane tetraacrylate; urethane acrylates such as urethane acrylate, urethane dimethyl acrylate, and urethane trimethyl acrylate; and other compounds such as acrylamide, acrylic acid, and dimethylacrylamide.

The polymerization in the present invention is most appropriately radical polymerization using potassium persulfate, but may be polymerization using ultraviolet rays or electron beams or redox polymerization. In polymerization using potassium persulfate, it is preferable to add 0.001 to 0.25 mass % of potassium persulfate and 0.001 to 0.5 mass % of a polymerization initiator. As the polymerization initiator, β-dimethylaminopropionitrile, N,N,N',N'-tetramethylethylenediamine, sodium sulfite, or the like is preferable.

The pellet block preparation section 2 comprises the forming frame 52 of producing a pellet block 60 by polymerizing the mixture, a heating device 53 of heating the forming frame 52, a transfer stage 54 of transporting the forming frame 52, and a removal device 56 of removing the pellet block 60 as main components.

The forming frame 52 is in the shape of a container in which the mixture is polymerized while reducing contact with oxygen. A plurality of the forming frames 52 are arranged on the transfer stage 54, and a predetermined amount of the mixture is introduced into each of the forming frames 52.

The material for the forming frame 52 is preferably a material that does not inhibit polymerization reaction of the mixture and has low wettability with the pellet block 60. For example, vinyl chloride, SUS, an acrylic resin, or the like is more preferable. The size of the forming frame 52 is preferably about 1 to 10 L in terms of removability and productivity.

The forming frame 52 preferably has a shape to have a ratio V/S of the volume V of the forming frame 52 to the bottom area S of the forming frame 52 of 10 to 100. By providing the pellet block with such a shape, the contact interface with oxygen (corresponding to the bottom area part) can be reduced, and the resistance when removing the block from the forming frame can also be reduced. Accordingly, entrapping immobilization pellets with highly stable quality can be efficiently produced. The shape of the forming frame 52 is preferably a cuboid or cube from the viewpoint of handling and yield, but is not limited thereto. The shape may be a cylinder or the like. In order to suppress contact with oxygen during polymerization, the forming frame preferably has a structure that can be closed with a lid 57 (see FIG. 2) or the like or a vertically long structure with a small opening surface.

The heating device 53 is provided in the forming frame 52. Thus, the mixture can be heated to or maintained at a temperature appropriate for polymerization reaction in the forming frame 52. Accordingly, the polymerization reaction rate of the mixture can be increased, and the pellet block 60 can be produced in a short time.

Specific examples of the heating device 53 include various heaters, but other devices that can maintain the mixture in the forming frame 52 at a predetermined temperature are also possible.

Figure 2:
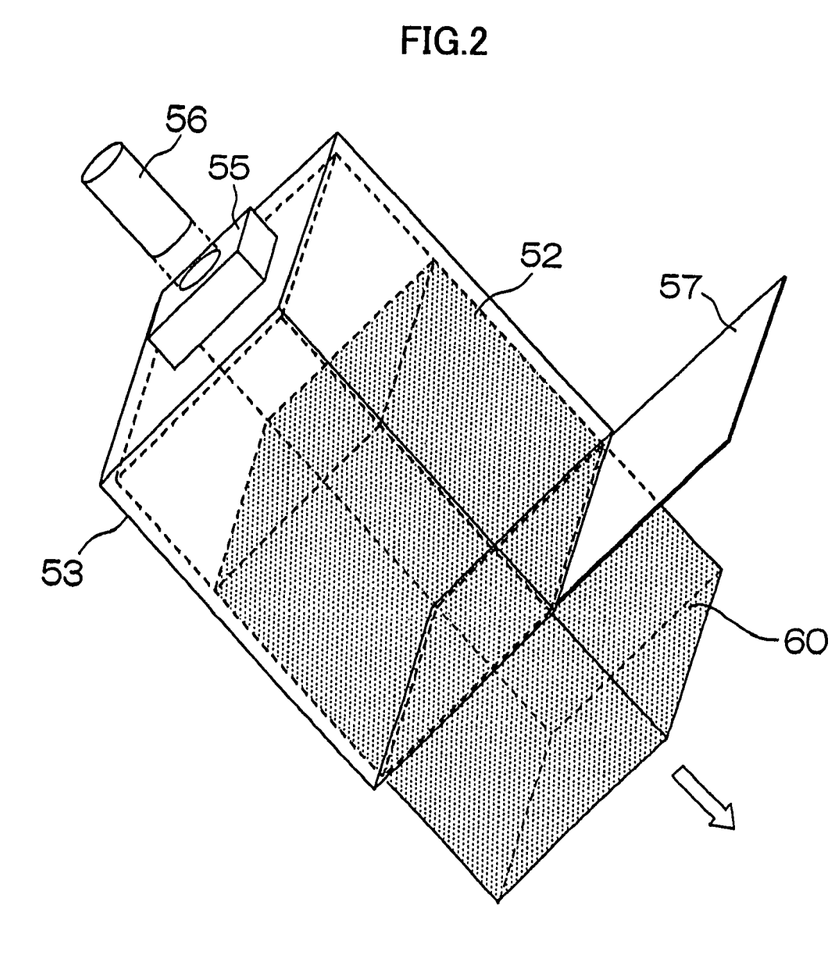
FIG. 2 is an oblique view showing the forming frame according to an embodiment of the present invention.

FIG. 2 is a schematic view of the forming frame 52 with an injection pipe 56 mounted. As shown in FIG. 2, the injection pipe 56 is communicated with the bottom of the forming frame 52 via a joint 55. When removing the pellet block 60, the forming frame 52 is inclined at about 45°, and air or water is injected into the forming frame 52 from the injection pipe 56 at a predetermined pressure (about 0.1 MPa) to pressurize the inside. The pellet block 60 is thus extruded from the forming frame 52. The injection pipe 56 may be provided on the forming frame 52, or may be mounted from the outside. The bottom of the forming frame 52 may be formed with a valve or a plug, for example, so that the frame can be communicated with the injection pipe 56 except when preparing the pellet block 60.

The pellet block 60 may be removed by a method of inclining the forming frame 52 and injecting an inert gas (such as nitrogen gas or air) or a liquid (such as water) into the forming frame 52 at a predetermined pressure, or by a method of opening a plug (not shown) provided on the bottom of the forming frame 52 and making the pressure on the bottom of the forming frame atmospheric. Alternatively, the pellet block 60 may be removed by injecting a liquid that can reduce wettability between the forming frame 52 and the pellet block 60 into the forming frame 52 to improve slip properties of the pellet block 60. After removing the pellet block 60, the forming frame 52 is used for polymerizing the mixture again.

Figure 3A:
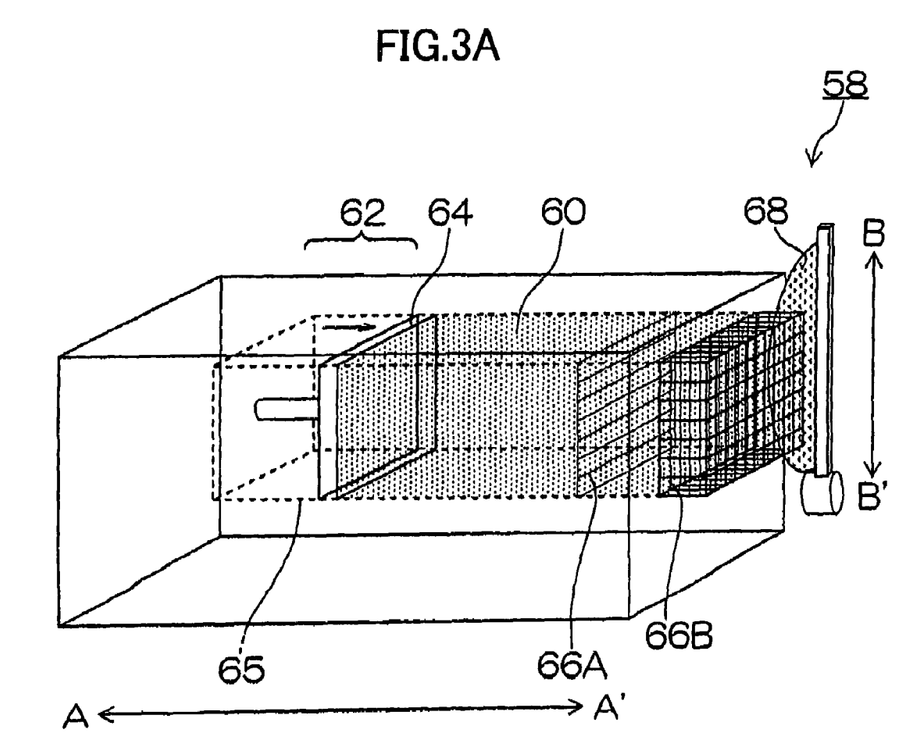
FIG. 3 is a side view showing the cutting unit according to an embodiment of the present invention.
Figure 3B:
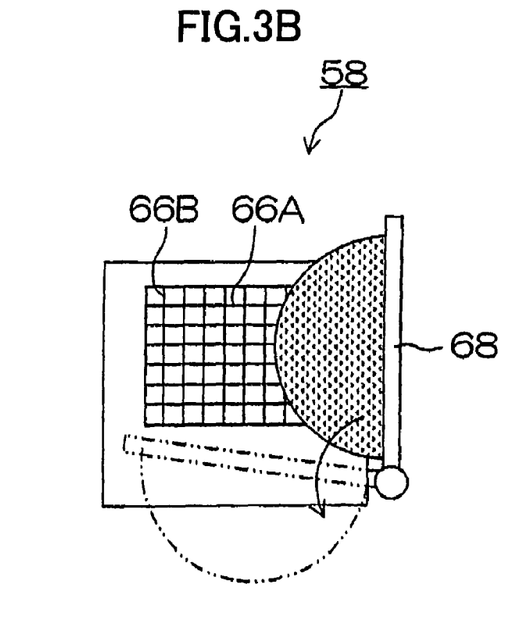

The pellet block cutting section 3 includes a cutting unit 58 comprising a transport device 62 and an extrusion board 64 which transport the pellet block 60 while fixing, a fixing stage 65 of fixing the pellet block 60, lattice-shaped cutting blades 66A, 66B, and a rotary cutting blade 68 as main components. FIG. 3A is a side view showing the cutting unit 58, and FIG. 3B is a plan view corresponding to FIG. 3A.

The fixing stage 65 has a shape of a groove in which the pellet block 60 is fixed when cutting the pellet block 60. The groove has almost the same width as in the pellet block 60, and the pellet block 60 is placed in the groove. The lattice-shaped cutting blades 66A, 66B are provided on the top of the groove. The pellet block 60 is transported through the fixing stage 65 to the lattice-shaped cutting blades 66A, 66B by the extrusion board 64.

The extrusion board 64 extrudes the pellet block 60 into the lattice-shaped cutting blades 66A, 66B at a predetermined speed. As shown in FIG. 3A, the extrusion board 64 is configured to be movable by the transport device 62 such as a ball screw mechanism or a cylinder mechanism which can control the transport speed, for example.

The lattice-shaped cutting blades 66A, 66B are formed by providing a plurality of cutting blades at predetermined intervals in the shape of lattices. In the lattice-shaped cutting blades 66A, 66B in FIGS. 3A and 3B, cutting blades lattice-shaped in the crosswise direction (A-A' direction) are combined with cutting blades lattice-shaped in the longitudinal direction (B-B' direction). As the lattice-shaped cutting blades 66A, 66B, wire saws or cutter blades arranged in the shape of lattices can be used. In the present embodiment, in order to produce 3 mm-square cubic entrapping immobilization pellets 70, lattice-shaped cutting blades provided at intervals of about 3 mm each are preferable. The pellet block 60 is cut into about 3 mm-narrow lattices with the lattice-shaped cutting blades 66A, 66B.

The rotary cutting blade 68 cuts the pellet block 60 with about 3 mm-narrow lattices perpendicular to the transport direction at a predetermined rotation speed.

A thin cutting blade having a thickness of 1 mm, for example, is used for the lattice-shaped cutting blades 66A, 66B or the rotary cutting blade 68.

Thus, the pellet block 60 is cut into lattices in the fixing stage 65, while the block is transported by the transport device 62 at a predetermined transport speed. The lattices are then cut into 3 mm-square cubes with the rotary cutting blade 68.

Next, the process for producing entrapping immobilization pellets using the production apparatus 10 in FIG. 1 will be described.

First, a raw material in the raw material tank 12 (such as activated sludge) and a chemical in the chemical tank 14 (such as an immobilizing agent solution) are mixed and fed into the stirring and extrusion unit 20 by driving the pumps 16, 18. Then, the mixture fed into the stirring and extrusion unit 20 is mixed with a chemical (such as a polymerization initiator) fed thereinto from the other chemical tank 22 by the pump 24, followed by stirring. The mixture is extruded into the forming frame 52 arranged on the transport stage 54 running (raw material mixing section 1).

Then, the mixture is polymerized into a gel in the forming frame 52 heated to or maintained at 20 to 30° C. In this case, the mixture contains an immobilizing agent, water, activated sludge, a polymerization initiator, a polymerization accelerator, and the like. Polymerization reaction proceeds for 10 to 60 minutes to produce a gelled pellet block 60. Thereafter, the forming frame is inclined at about 45°. At the same time, the removal device 56 is mounted on the bottom of the forming frame 52, and air is injected into the forming frame 52 at a pressure of about 0.1 MPa. Thus, the gelled pellet block 60 is smoothly removed from the forming frame 52 while maintaining the formed shape in the forming frame 52 (pellet block preparation section 2).

Next, the pellet block 60 removed from the forming frame 52 is transported to the cutting unit 58 and stored in the fixing stage 65. The pellet block 60 is cut into about 3 mm-wide lattices with the lattice-shaped cutting blades 66A, 66B, while being transported by the transport device 62 and the extrusion board 64, and then the lattices are cut substantially into cubes with the rotary cutting blade 68. 3 mm-square cubic entrapping immobilization pellets 70 are thus produced (pellet block cutting section 3).

As described above, the process for producing entrapping immobilization pellets of the present invention carries out polymerization in the forming frame in order to reduce the contact interface with air, and accordingly can produce a pellet block with highly stable quality inexpensively. By cutting the pellet block with the lattice-shaped cutting blades and the rotary cutting blade while fixing, a large amount of uniform and substantially cubic pellets can be produced at high speed.

EXAMPLES

Examples of the present invention will be described below. However, the present invention is not limited to the examples.

1) The relation between the type of forming method and the amount of COD eluted, 2) the V/S ratio as a shape condition of the forming frame, 3) the pellet deformation ratio, 4) prepolymer properties (molecular weight and concentration), and 5) polymerization conditions (polymerization time and temperature) were examined using the production apparatus 10 of the present invention shown in FIG. 1. As the pellet materials, those of FIG. 1 were mainly used.

TABLE 1

| Type of material | Content |
|---|---|
| Activated sludge | MLSS 30000 mg/L |
| Number of nitrifying bacteria | $5 \times 10^6$ cells/mL |
| Immobilizing agent | Polyethylene glycol dimethacrylate |
| Polymerization initiator | Potassium persulfate: 0.025 mass % |
| Polymerization accelerator | N,N,N',N'-tetramethylethylenediamine: 0.05 mass % |

1) The Relation Between the Type of Forming Method and the Amount of COD Eluted

Entrapping immobilization pellets (hereinafter referred to as "pellets") were prepared using the process and the apparatus for producing entrapping immobilization pellets of the present invention under the following conditions. First, a prepolymer having a molecular weight of 9,000 as an immobilizing agent was dissolved in water at a prepolymer concentration per pellet of 10 mass % to prepare an immobilizing agent solution. Next, the immobilizing agent solution and activated sludge in Table 1 were put into a 4 L-volume forming frame 52 having a V/S ratio of 40 to prepare a mixture, and then a polymerization initiator and a polymerization accelerator in Table 1 were added to the mixture. The mixture was polymerized at a polymerization temperature of 20° C. for a polymerization time of 30 minutes to prepare a pellet block. The pellet block was cut into 3 mm-square cubes to prepare pellets (pellets produced by the block forming of the present invention).

Further, pellets were prepared by conventional sheet forming under the same conditions except for the forming method (pellets produced by conventional sheet forming).

The pellet strengths of the pellets prepared by the respective forming methods were measured and compared. Using a rheometer, the pellet strengths were measured as a compression force per unit area when compressing entrapping immobilization pellets with a certain force to break the pellet gel (meaning that, when the pellet strength is 7 kg/cm², the pellets are broken down by applying pressure above the compression force). Next, the pellets were added to 425 mL of tap water at a true volume ratio of 15% to provide 500 mL of a mixture, which was then stirred with a stirrer in a beaker for 30 minutes. Then, the COD concentrations were measured for the pellets prepared by the respective forming methods using a method of measuring the oxygen demand by potassium permanganate at 100° C. in accordance with JIS K 0102 to calculate the amounts of COD eluted (unit: 1 mg/L).

TABLE 2

| Item | Block forming | Sheet forming |
|---|---|---|
| Compression strength (kg/cm²) | 7.3 | 4.1 |
| Amount of COD eluted (mg/L) | 180 | 720 |

As is clear from Table 2, the block forming attained a compression strength about 1.8 times of that attained by the conventional sheet forming, and polymerization was carried out well by the block forming. As shown in Table 2, the block forming of the present invention only attained a considerably small amount of COD eluted about ¼ of that attained by the conventional sheet forming. Therefore, it was found that unpolymerized parts of the pellets can be reduced by the block forming of the present invention.

2) The V/S Ratio as a Shape Condition of the Forming Frame

The shape condition of the forming frame which can reduce the contact interface with oxygen and allows easy removal from the forming frame was examined. A pellet block was prepared in the same manner as in 1). The pellet strength was measured by the same method as in 1). The removal time was defined as a period during which the forming frame was inclined at about 45° in the horizontal direction after polymerization, air was injected into the bottom of the forming frame at a pressure of 0.1 MPa, and the pellet block was removed.

Figure 4:
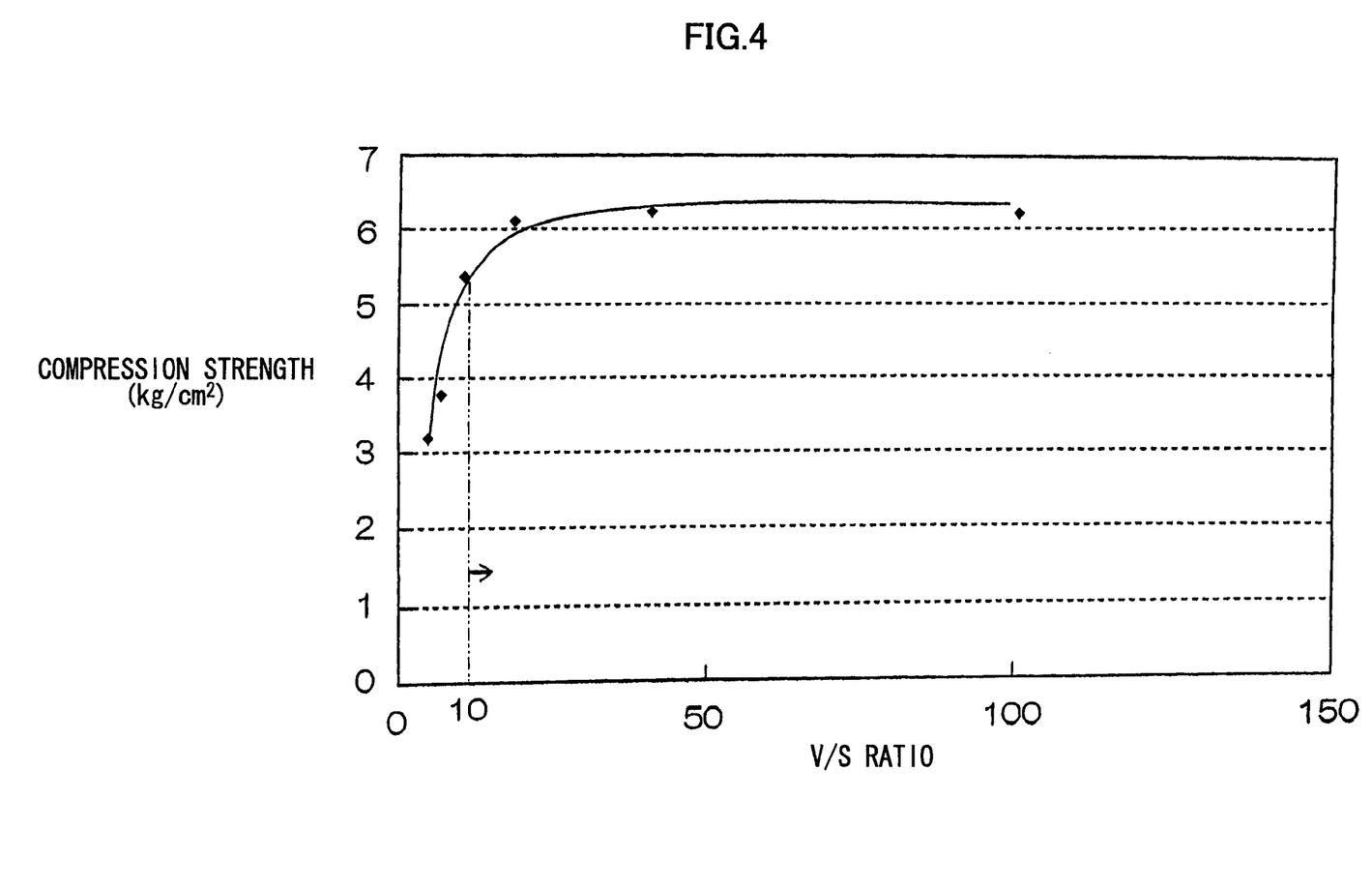
FIG. 4 is a graph showing the relation between the V/S ratio and the pellet strength in an example of the present invention.
Figure 5:
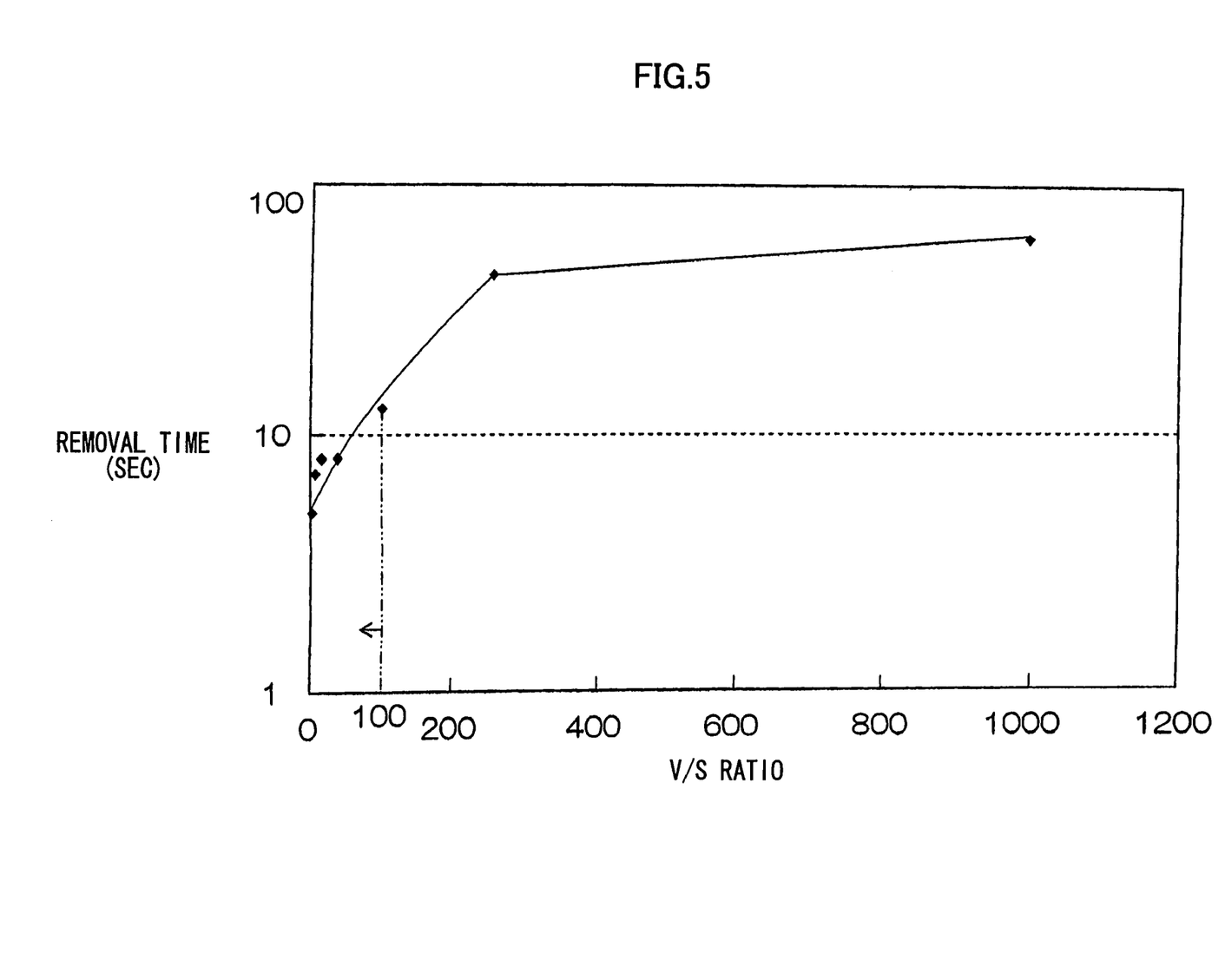
FIG. 5 is a graph showing the relation between the V/S ratio and the removal time in an example of the present invention.

According to the relation between the V/S ratio and the pellet strength (compression strength) in the forming frame in FIG. 4, when the V/S ratio was less than 10, the interface in contact with oxygen in the forming frame during polymerization had a large area, and the pellet strength tended to be reduced. On the other hand, it was found that the pellet strength was high almost in a stable manner at a V/S ratio of 10 or more. According to the relation between the V/S ratio and the removal time in FIG. 5, when the V/S ratio was more than 100, the forming frame had wall resistance increased, making it difficult to remove the pellet block from the forming frame. Therefore, it was found that a V/S ratio of 10 to 100 is an appropriate condition in which polymerization can be carried out well and the pellet block can be easily removed.

3) Pellet Deformation Ratio

Next, the relation between removability from the forming frame and the pellet deformation ratio was examined. A pellet block was prepared in the same manner as in 1). Using a rheometer, the pellet deformation ratio was calculated as a ratio of the pellet thickness immediately before breakdown of entrapping immobilization pellets by compressing the pellets with a certain force to the initial pellet thickness. The removal time was defined as a period during which the forming frame was inclined at about 45° in the horizontal direction after polymerization for 30 minutes, air was injected into the bottom of the forming frame at a pressure of 0.1 MPa, and the pellet block was removed.

Figure 6:
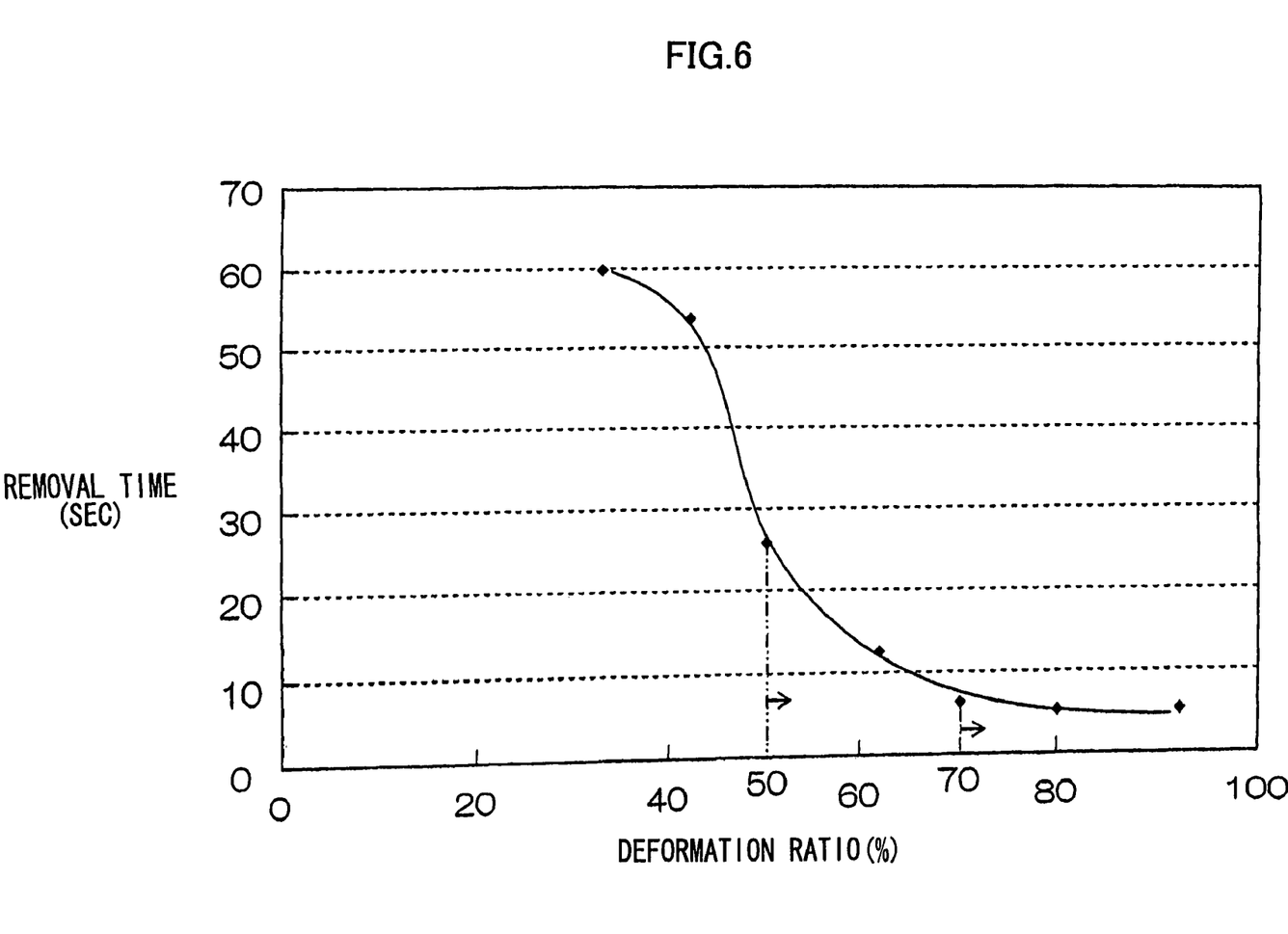
FIG. 6 is a graph showing the relation between the pellet deformation ratio and the removal time in an example of the present invention.

As is clear from FIG. 6, the removal time was considerably reduced at a pellet deformation ratio of 50% or more, and the pellet block could be removed in a short time almost certain at a pellet deformation ratio of 70% or more. Accordingly, it was found that the pellet block is hard and fragile at a deformation ratio of less than 50%, and thus it takes a long time to remove the pellet block and the production efficiency is decreased.

Therefore, it was found that the pellet deformation ratio is preferably 50% or more, and more preferably 70% or more.

4) Prepolymer Properties (Molecular Weight and Concentration)

It was found in 2) that the pellet deformation ratio is related with the prepolymer molecular weight and concentration of the immobilizing agent. Then, the relation between the prepolymer molecular weight and concentration and the pellet deformation ratio was examined. A pellet block was prepared on conditions that the prepolymer molecular weight was 500 to 20,000 and the prepolymer concentration was 0 to 20 mass %, using a polymerization initiator and a polymerization accelerator in Table 1 at a polymerization temperature of 20° C. for a polymerization time of 30 minutes. Using a rheometer, the pellet deformation ratio was calculated as a ratio of the pellet thickness immediately before breakdown of entrapping immobilization pellets by compressing the pellets with a certain force to the initial pellet thickness.

Figure 7:
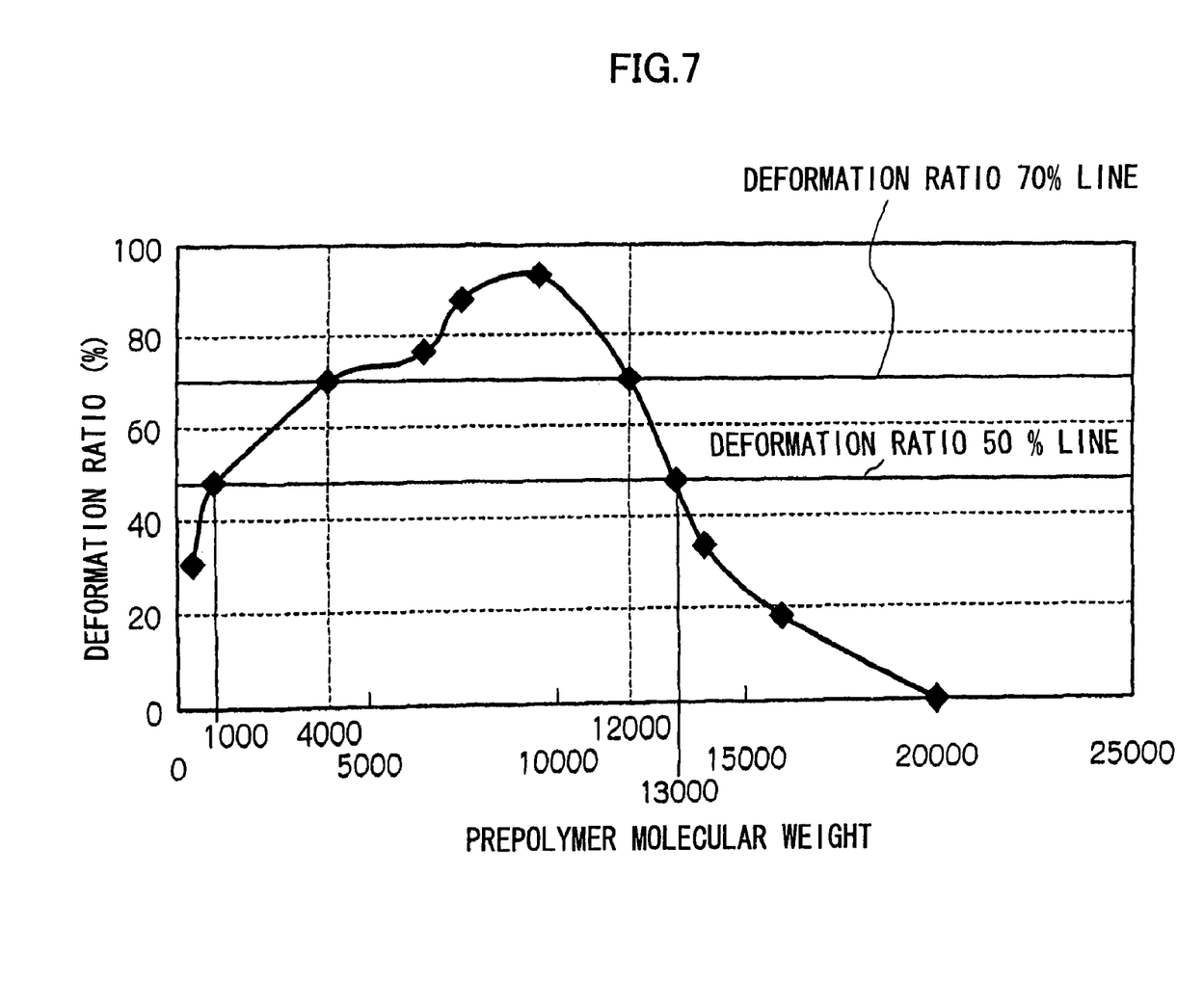
FIG. 7 is a graph showing the relation between the prepolymer molecular weight and the pellet deformation ratio in an example of the present invention.

As is clear from FIG. 7, when the prepolymer concentration was 10 mass %, the pellet deformation ratio was 50% or more and the pellet block could be easily removed if the prepolymer molecular weight was 1,000 to 13,000, and the pellet deformation ratio was 70% or more and the pellet block could be more easily removed if the prepolymer molecular weight was 4,000 to 12,000.

Figure 8:
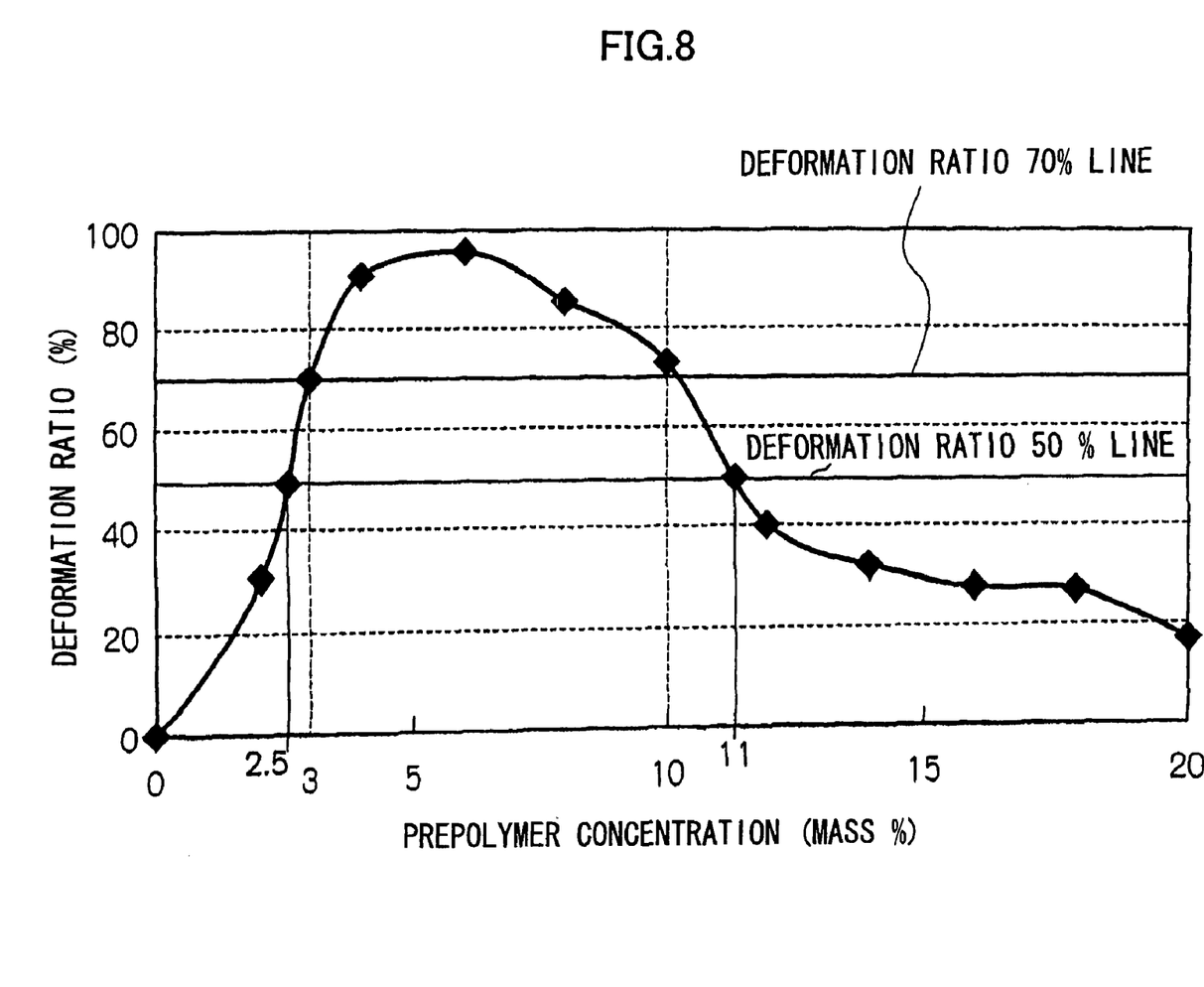
FIG. 8 is a graph showing the relation between the prepolymer concentration and the pellet deformation ratio in an example of the present invention.

As is clear from FIG. 8, when the prepolymer molecular weight was 9,000, the pellet deformation ratio was 50% or more and the pellet block could be easily removed if the prepolymer concentration was 2.5 to 11 mass %, and the pellet deformation ratio was 70% or more and the pellet block could be more easily removed if the prepolymer concentration was 3 to 10 mass %.

5) Examination on Polymerization Conditions (Polymerization Time and Temperature)

Polymerization conditions having an influence on the pellet strength were examined. A pellet block was prepared from a prepolymer having a molecular weight of 9,000 and a polymerization initiator and a polymerization accelerator in Table 1 at a polymerization temperature of 20° C. for a polymerization time of 10 to 70 minutes to examine the influence by the polymerization time. Then, the removal time was measured by the same method as in 3).

Figure 9:
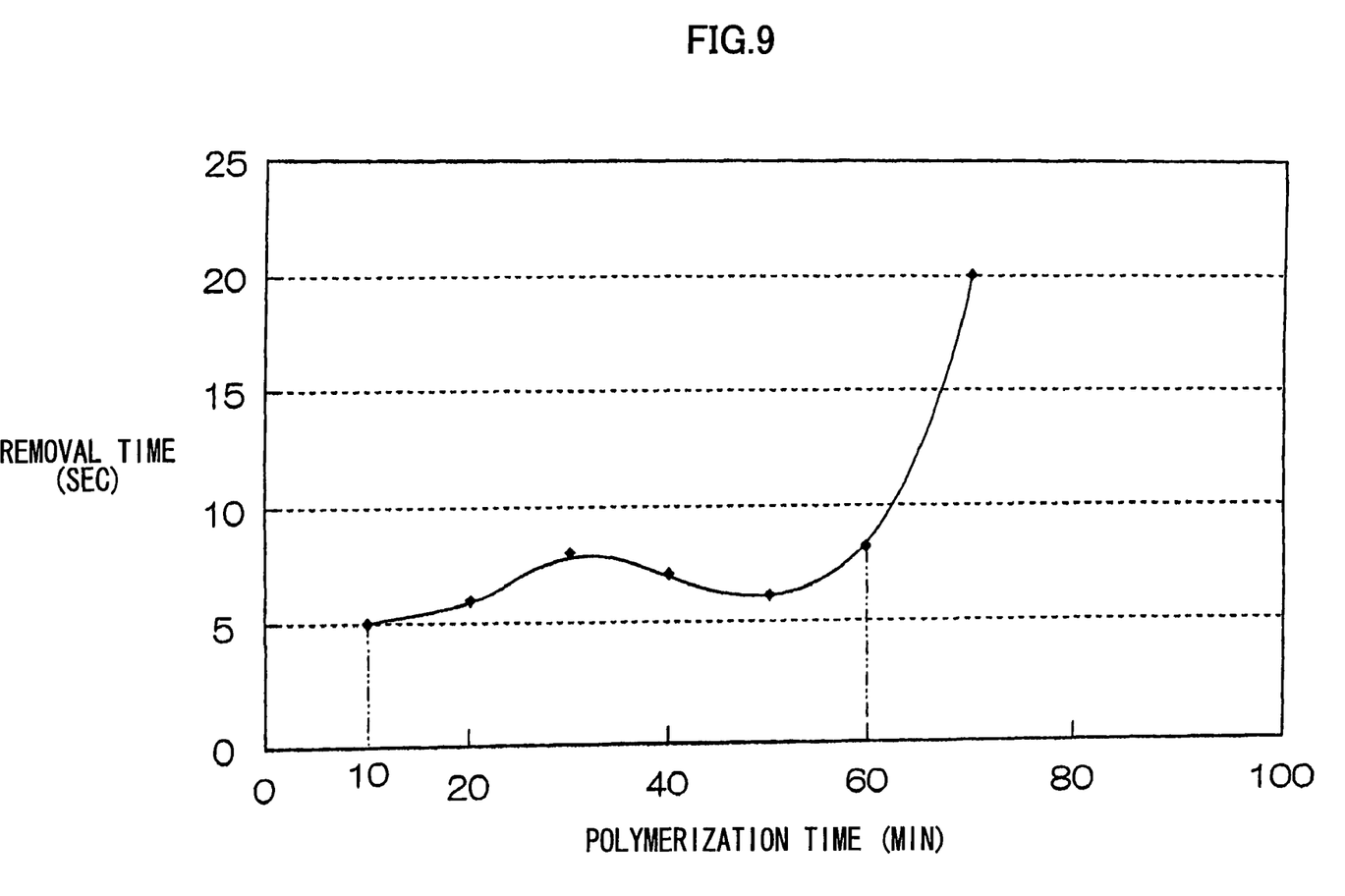
FIG. 9 is a graph showing the relation between the polymerization time and the removal time in an example of the present invention.

As shown in FIG. 9, when the polymerization time was shorter than 10 minutes, polymerization was insufficient and the pellet block could not be removed. When the polymerization time was 60 minutes or longer, it took a long time to remove the pellet block. When the polymerization time was 80 minutes or longer, the pellet block could not be removed. Therefore, when the polymerization time is 10 to 60 minutes, polymerization can be sufficiently carried out, and the removal time can be reduced.

Further, a pellet block was prepared using a prepolymer having the same molecular weight at a polymerization temperature of 5 to 40° C. for a polymerization time of 30 minutes to examine the influence by the polymerization temperature. Then, the pellet strength was measured by the same method as in 1).

Figure 10:
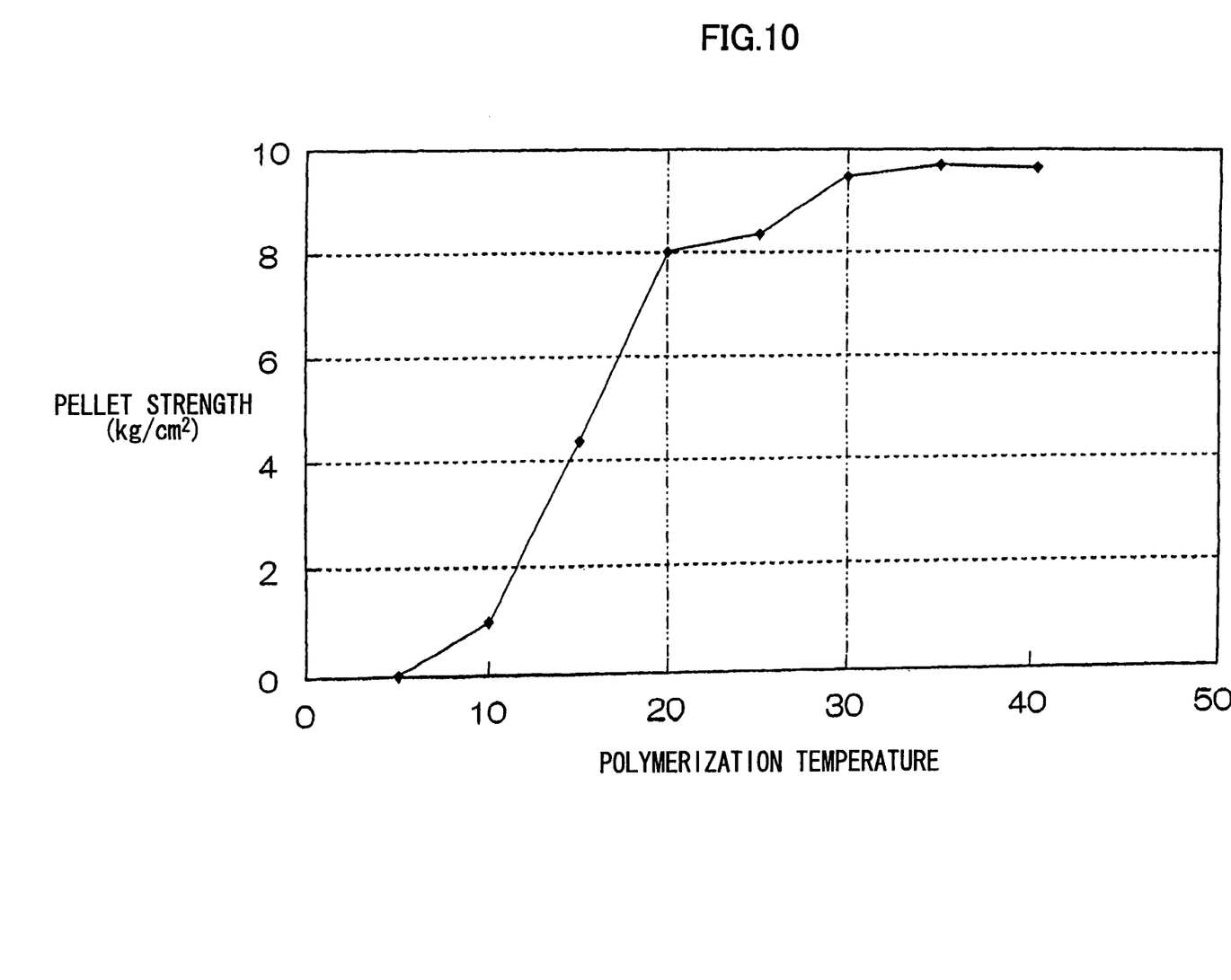
FIG. 10 is a graph showing the relation between the polymerization temperature and the pellet strength in an example of the present invention.

As shown in FIG. 10, it was found that, when the polymerization temperature was 20° C. or higher, the pellet strength was high almost in a stable manner. On the other hand, when the polymerization temperature was lower than 20° C., the pellet strength was considerably reduced as the temperature was lowered. In particular, when the temperature was 10° C. or lower, polymerization was insufficient. Even when the polymerization temperature was higher than 30° C., the pellet strength almost did not change. Therefore, it was found that the polymerization temperature is preferably 20° C. or more, and more preferably 20 to 30° C. when using an immobilizing agent having a molecular weight of 9,000.

As described above, since the area of the contact interface with oxygen is reduced during polymerization by applying the present invention, a large amount of entrapping immobilization pellets with highly stable quality can be produced inexpensively by high-speed treatment.

What is claimed is:

1. An apparatus for producing pellets containing entrapped and immobilized microorganisms, comprising:
   at least one forming frame configured to hold a mixture containing microorganisms, polymerization initiator, and an immobilizing agent solution where the mixture polymerizes into a gel in the forming frame to prepare a block, the forming frame having an interior volume V and a bottom area S;
   a raw material tank that stores microorganisms;
   a first chemical tank that stores the immobilizing agent solution;

a second chemical tank that stores a polymerization initiator;

a stirring and extrusion unit that mixes microorganisms from the raw material tank with immobilizing agent solution from the first chemical tank and polymerization initiator from the second chemical tank to form a mixture, and extrudes the mixture into the forming frame where the mixture polymerizes into a gel to form the block;

a transfer stage that transports the at least one forming frame containing the block to a removal device for removing the block from the forming frame; and a cutting unit for receiving the block from the forming frame to cut the block into pellets.

2. The apparatus according to claim 1, further comprising a heating device connected to the forming frame.

3. The apparatus according to claim 1, wherein the removal device comprises:

an extrusion device configured to extrude the block from the forming frame, wherein the extrusion device is connected to a bottom of the forming frame via a joint, at least one inclination device for inclining the forming frame, and a pressurizing device for pressurizing an inside of the forming frame.

4. The apparatus according to claim 1, wherein the cutting device comprises:

lattice-shaped cutting blades for cutting the block into lattices; and a rotary cutting blade for cutting the block cut into lattices substantially into cubes, the blade provided downstream of the lattice-shaped cutting blades.

5. The apparatus according to claim 3, wherein the cutting device comprises:

lattice-shaped cutting blades for cutting the block into lattices; and a rotary cutting blade for cutting the block cut into lattices substantially into cubes, the blade provided downstream of the lattice-shaped cutting blades.

6. The apparatus according to claim 4, further comprising:

a control device configured to control a transport speed of the block and a rotation speed of the rotary cutting blade, so that the entrapping immobilization pellets after cutting are substantially cubes.

7. The apparatus according to claim 5, further comprising:

a control device configured to control a transport speed of the block and a rotation speed of the rotary cutting blade, so that the pellets after cutting are substantially cubes.

8. The apparatus according to claim 1, wherein the forming frame is substantially a cuboid.

9. The apparatus according to claim 3, wherein the forming frame is substantially a cuboid.

10. The apparatus according to claim 4, wherein the forming frame is substantially a cuboid.

11. The apparatus according to claim 5, wherein the forming frame is substantially a cuboid.

12. The apparatus according to claim 6, wherein the forming frame is substantially a cuboid.

13. The apparatus according to claim 7, wherein the forming frame is substantially a cuboid.

* * * * *